United States Patent [19]

Buder et al.

[11] 4,337,205
[45] Jun. 29, 1982

[54] NITROGEN CONTAINING ALKOXYSILANE AND PROCESS FOR ITS PRODUCTION

[75] Inventors: Wolfgang Buder, Rodenbach; Siegfried Wolff, Bornheim-Merten; Peter Kleinschmit, Hanau, all of Fed. Rep. of Germany

[73] Assignee: Degussa Aktiengesellschaft, Frankfurt, Fed. Rep. of Germany

[21] Appl. No.: 182,313

[22] Filed: Aug. 28, 1980

[30] Foreign Application Priority Data

Sep. 1, 1979 [DE] Fed. Rep. of Germany ....... 2935454

[51] Int. Cl.$^3$ .................. C07C 117/04; C07C 118/04
[52] U.S. Cl. .................................. 260/349; 556/414; 568/13
[58] Field of Search ........................................ 260/349

[56] References Cited

U.S. PATENT DOCUMENTS

| | | | |
|---|---|---|---|
| 3,284,421 | 11/1966 | Breslow | 260/80.5 |
| 3,526,644 | 9/1970 | Suzuki | 260/349 |
| 3,547,843 | 12/1970 | Suzuki | 260/349 |
| 3,697,551 | 10/1972 | Thomson | 260/448.2 B X |
| 3,705,911 | 12/1972 | Thomson | 260/349 |
| 3,706,592 | 12/1972 | Thomson | 260/349 X |
| 3,821,218 | 6/1974 | Berger | 260/248 NS |

FOREIGN PATENT DOCUMENTS 2165198 8/1972 Fed. Rep. of Germany .

OTHER PUBLICATIONS

Kozyukov et al., Zh. Obshch. Khim. (1968), vol. 38, No. 5, pp. 1179–1185.
Buder et al., Spectrochimica Acta., vol. 29A, pp. 1429–1438, (1972).
Staudinger et al., Helvetica Chimica Acta., vol. 2, pp. 635–646, (1919).
Lieber et al., Chemical Reviews, vol. 65, pp. 377–378, 379–384, (1965).
Gololobov et al., Tetrahedron, vol. 37, (1981), pp. 437, 438, 462–472.

Primary Examiner—Joseph Paul Brust

[57] ABSTRACT

There are prepared nitrogen containing alkoxysilanes of the formula $(RO)_{3-n}(CH_3)_nSi(CH_2)_mNHCON_3$ in which R is an alkyl group having 1 to 3 carbon atoms, n is 0, 1 or 2 and m is 1, 2 or 3 by a process comprising dissolving in an inert solvent an isocyanate group containing silane of the formula $(RO)_{3-n}(CH_3)_nSi(CH_2)_mN=C=O$ in which R, n and m are as defined above and reacting the silane with a water free hydrogen nitride or with hydrogen halide and an alkali metal-alkaline earth metal-, or ammonium azide at a temperature between 0° C. and the boiling point of the inert solvent. The compounds are useful in making phosphinimines.

6 Claims, 4 Drawing Figures

NITROGEN CONTAINING ALKOXYSILANE AND PROCESS FOR ITS PRODUCTION

BACKGROUND OF THE INVENTION

The invention is directed to new nitrogen containing alkoxysilanes and their production.

There are known isocyanate group containing organosilicon compounds of various structures. Thus there can be produced e.g. 3-trimethoxysilylpropylisocyanate $(CH_3O)_3Si\ C_3H_6NCO$ according to Berger U.S. Pat. No. 3,821,218 or diethoxymethylsilylmethylisocyanate $(C_2H_5O)_2\ CH_3Si\ CH_2NCO$ according to V. P. Kozynkov, Zh. Obshch. Khim. 1968, Vol. 38 (5), pages 1179-85. The entire disclosures of Berger and Kozynkov are hereby incorporated by reference and relied upon.

Furthermore there are known silanes which have the arylsulfonylazide groups. Thus, e.g. trimethoxysilylamylsulfonylazide or trimethoxysilyl-cyclohexylsulfonylazide can be produced according to Thomson U.S. Pat. No. 3,697,551.

Furthermore organosilicon compounds are known which have the azidoformate group of the formula $-OCON_3$, as e.g. trimethoxysilylethyl azidoformate, triethoxysilylpropylazidoformate, etc. (German OS 2165198). The azidoformates can also be produced by reaction of a chloroformate with an excess of an alkali azide (see also U.S. Pat. No. 3,284,421).

SUMMARY OF THE INVENTION

The compounds of the invention are silylalkylcarbamidazides of the formula $(RO)_{3-n}(CH_3)_nSi(CH_2)_mNHCON_3$ in which R is an alkyl group having 1 to 3 carbon atoms, n is 0, 1 or 2 and m is 1, 2 or 3. They are produced according to the following two formula equations from the corresponding isocyanates according to the process known of itself (Spectrochimica Acta, Vol. 29A, pages 1429-1438 (1973).

(a) 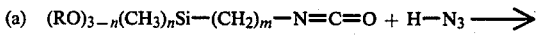

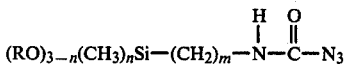

(b) 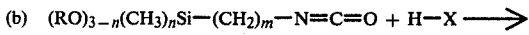

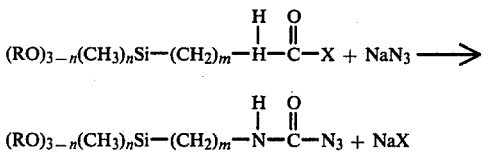

The designation X means halogen e.g., fluorine or iodine or preferably chlorine or bromine. In place of the stated alkali metal sodium there can also be employed other alkali metal azides as especially potassium azide or ammonium azide. There can also be used the alkaline earth metal salts as e.g. magnesium-, calcium- and barium azides.

As starting isocyanates there can be used for example:
3-trimethoxysilylpropyl isocyanate,
trimethoxysilylmethyl isocyanate,
2-trimethoxysilylethyl isocyanate,
3-tripropoxysilylpropyl isocyanate,
2-triisopropoxysilylethyl isocyanate,
triethoxysilylmethyl isocyanate,
diethoxymethylsilylmethyl isocyanate,
3-diethoxymethylsilylpropyl isocyanate,
dipropoxymethylsilylmethyl isocyanate,
ethoxydimethylsilylmethyl isocyanate.

Examples of compounds within the present invention include:
3-trimethoxysilylpropylcarbamidazide,
trimethoxysilylmethylcarbamidazide,
2-trimethoxysilylethylcarbamidazide,
3-tripropoxysilylpropylcarbamidazide,
2-triisopropoxysilylethylcarbamidazide,
triethoxysilylmethylcarbamidazide,
diethoxymethylsilylmethylcarbamidazide,
3-diethoxymethylsilylpropylcarbamidazide,
3-dimethoxymethylsilylpropylcarbamidazide,
dipropoxymethylsilylmethylcarbamidazide,
dipropoxymethylsilylmethylcarbamidazide, and
ethoxydimethylsilylmethylcarbamidazide.

As solvents there can be used inert solvents which are liquid organic compounds at normal temperatures, at least partially dissolve the starting materials, do not coreact in the reaction and preferably do not dissolve the alkali metal halide or the like byproduct in order that these suitably precipitate. Such solvents especially include ethers such as diethyl ether, diisopropyl ether, di-n-propyl ether, methyl ethyl ether, ethyl propyl ether, 1,2-dimethoxyethane and the like; as well as chlorohydrocarbons, e.g. chloroalkanes such as, e.g. methylene chloride, 1,2-dichloroethane, 1,1-dichloroethane, carbon tetrachloride and chloroform. However, there can also be used acetonitrile or other aprotic solvents such as dimethylsulfoxide, dimethyl formamide or ketones, such as e.g. acetone or methyl ethyl ketone.

The temperature is not particularly critical and can vary for example between 0° C. and the boiling point of the inert solvent.

The azidosilanes of the invention can be used as intermediate products. Thus e.g., they can be used to produce phosphinimines according to Staudinger (see, e.g. Helv. Chim. Acta, Vol. 2, page 635 (1919). The entire disclosure of the Helv. Chim. Acta article is hereby incorporated by reference and relied upon.

Unless otherwise indicated all parts and percentages are by weight. The process can comprise, consist essentially of or consist of the stated steps with the materials set forth.

DETAILED DESCRIPTION OF THE INVENTION

Example 1

There were present in a standard apparatus equipped with an internal thermometer, stirrer and dropping funnel 1.0 mole of $(CH_3O)_3SiC_3H_6NCO$ (205.3 grams; $n_D^{25}$ 1.4186) diluted with 150 ml of absolute diethyl ether at 0° C. To this mixture there were dropped in with stirring within 30 minutes 1.05 moles of water free hydrogen nitride HN₃ (45.2 grams in 100 ml of diethyl ether). Thereby the temperature increased to the reflux temperature of the diethyl ether. After the end of the dropping the diethyl ether was drawn off in a vacuum. The remaining liquid (243.5 grams) was identified through NMR-, IR- and elemental analysis as 3-trimethoxy-silylpropylcarbamidazide. The yield was 98.1%.

Figure 1:
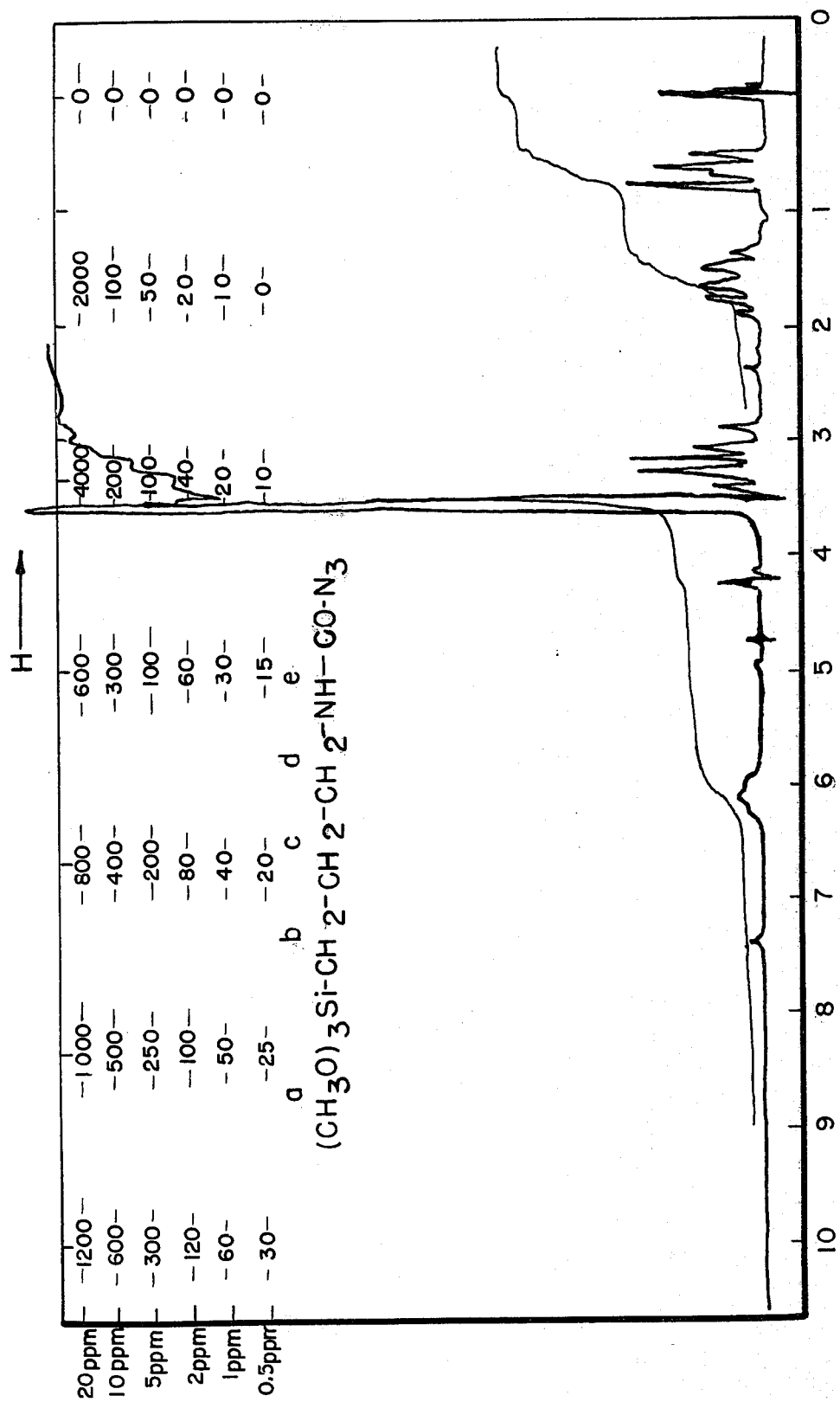
FIG. 1, is a NMP spectrum of the compound prepared in Example 1.
Figure 2:
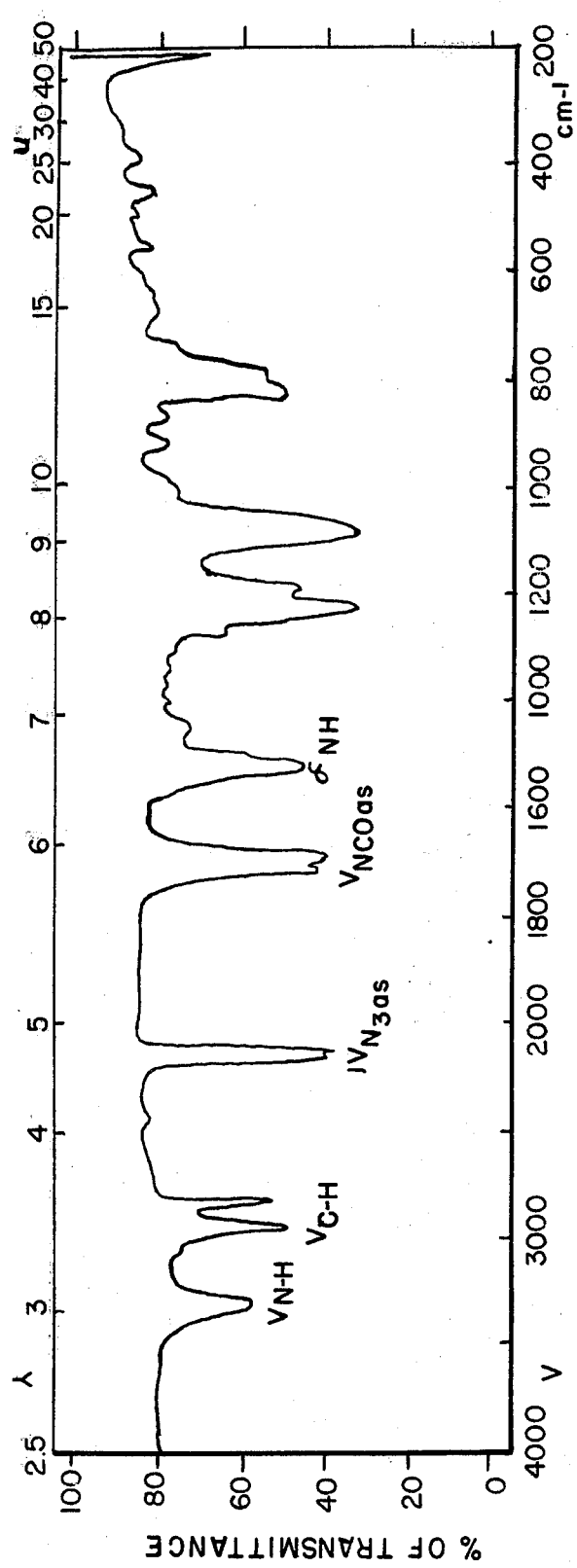
FIG. 2 is an IR spectrum of the compound in Example 1.

| Elemental analysis (in weight percent) | | | |
|---|---|---|---|
| | C | H | N |
| Calculated: | 33.86 | 6.46 | 22.56 |
| found: | 33.49 | 6.49 | 22.38 |
| Refractive index: | $n_D^{25} = 1.4574$ | | |
| FIG. 1: | 60 MHz NMR-Spectrum and | | |
| FIG. 2: | IR spectrum of the compound produced | | |

Example 2

In the manner described in Example 1, 1.0 mole of $(CH_3O)_3Si—CH_2NCO$ (177.3 grams; $n_D^{25}=1.4060$) were reacted with 1.05 mole of water free HN₃ (45.2 grams). The liquid remaining behind after drawing off the solvent according to NMR-, IR- and elemental analysis was trimethoxysilyl-methylcarbamidazide. The yield was 214.6 grams (97.4%).

Figure 4:
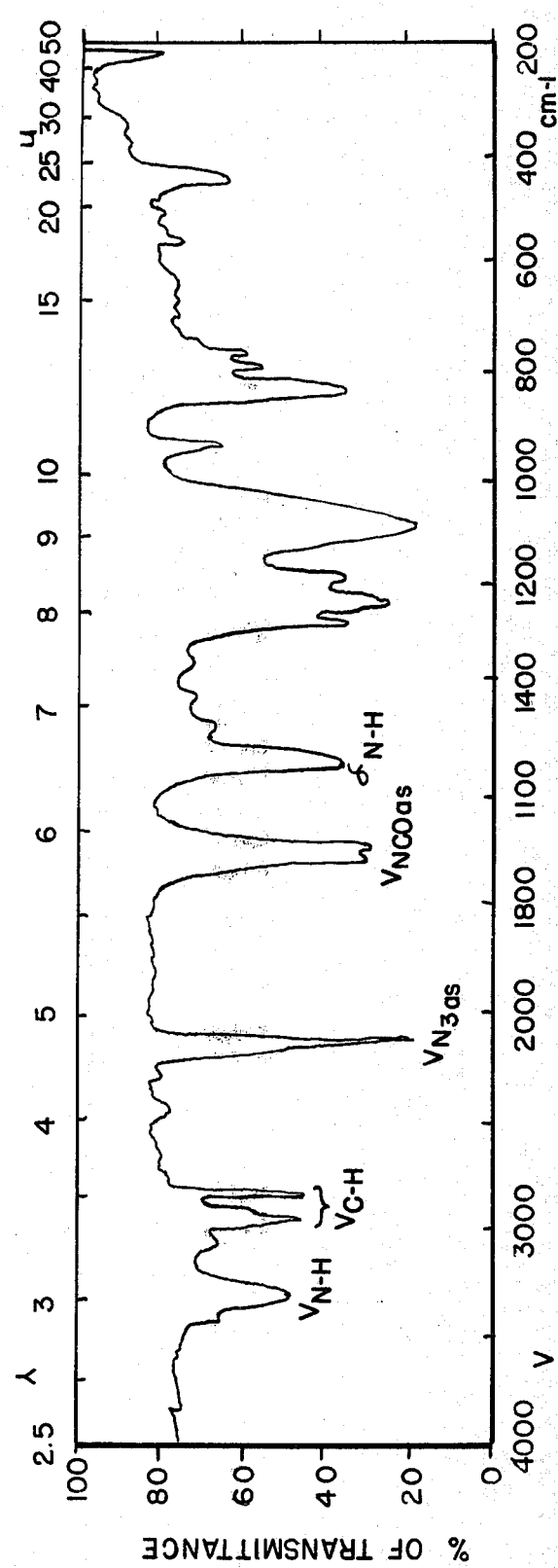
FIG. 4 is the IR spectrum of the compound prepared in Example 2.
Figure 3:
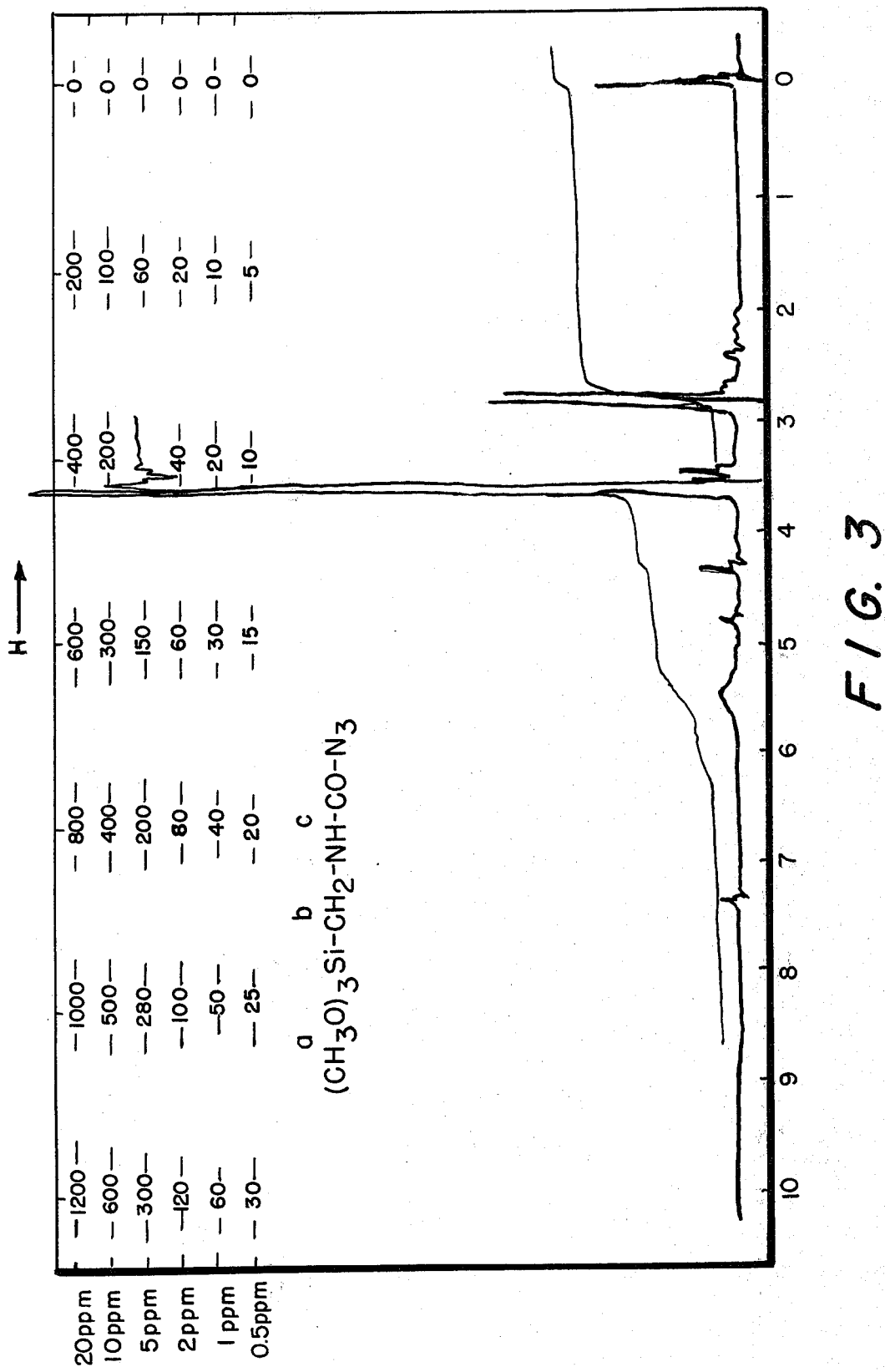
FIG. 3 is the NMR spectrum of the compound prepared in Example 2.

| Elemental analysis (in weight percent) | | | |
|---|---|---|---|
| | C | H | N |
| Calculated: | 27.27 | 5.49 | 25.43 |
| found: | 26.97 | 5.45 | 25.16 |
| Refractive index: | $n_D^{25} = 1.4602$ | | |
| FIG. 3: | 60 MHz NMR-Spectrum and | | |
| FIG. 4: | IR-Spectrum of the silane produced | | |

Example 3

In the apparatus described in Example 1 which now was additionally provided with a gas inlet tube there were present 1.0 mole of $(CH_3O)_3SiC_3H_6NCO$ (205.3 grams) diluted with 150 ml of 1,2-dichloroethane. Dry hydrogen chloride was led into this mixture at 0° C. until $\gamma_{as}NCO$ was no longer observed in the IR spectrum, i.e., until the corresponding carbamic acid chloride had completely formed. There were introduced into this solution 1.20 moles of dry, pulverized NaN₃ (78.0 grams) and the mixture stirred for 24 hours at 30° C. Then the solution was freed from precipitated NaCl and excess NaN₃ by filtration. After drawing off the solvent there remained behind 3-trimethoxysilylpropyl-carbamidazide in a yield of 92.4% (229.4 grams). The refractive index was $n_D^{25}=1.4575$.

For the two 60 MHZ H¹-NMR-spectrum represented in FIGS. 1 and 3, plotted with an NMR-spectrometer Type EM 360A of Varian Associates, Palo Alto, Calif., U.S.A., the following working directions apply: solvent CDCl₃: Temperature 37° C., Sweepwidth 4 Hz; R.F. field 0.05 mG; Registering time 250 seconds; Registering region 500 Hz; spectrum amplitude 10/9 or 10/10. Internal standard was tetramethylsilane ($\delta$ value=0). The integration curve which in each case is also represented belongs to the curve of the NMR spectrum. FIG. 1 shows the 1 H-NMR spectrum of $(CH_3O)_3Si—C_3H_6—NH—CON_3$ whose resonance signal and whose integration of the stated formula clearly can be coordinated; the same is true for $(CH_3O)_3SiCH_2NHCON_3$ and FIG. 3.

The IR absorptions of the IR spectra 2 and 4 was in the region 4000 cm⁻¹ to 1400 cm⁻¹, only this region is strongly asserted for the carbamidazide, of the correspondingly correlated vibrations. The IR spectra were plotted with an IR grating spectrophotometer PE 325 of Perkin-Elmer.

What is claimed is:

1. A nitrogen containing alkoxysilane of the formula

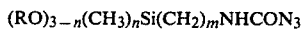
$(RO)_{3-n}(CH_3)_nSi(CH_2)_mNHCON_3$ in which R is an alkyl group having 1 to 3 carbon atoms, n is 0, 1 or 2 and m is 1, 2 or 3.

2. An alkoxysilane according to claim 1 where n is 0.
3. An alkoxysilane according to claim 2 where R is methyl.
4. An alkoxysilane according to claim 3 where m is 1.
5. An alkoxysilane according to claim 3 where m is 3.
6. An alkoxysilane according to claim 1 where n is 1 or 2.

* * * * *